United States Patent
Matsuda (10) Patent No.: US 9,125,614 B2
(45) Date of Patent: Sep. 8, 2015

(54) ULTRASONIC PROBE AND ULTRASONIC IMAGE DIAGNOSTIC DEVICE

(75) Inventor: Hiroshi Matsuda, Gifu (JP)

(73) Assignee: Seiko Epson Corporation, Tokyo (JP)

( * ) Notice: Subject to any disclaimer, the term of this patent is extended or adjusted under 35 U.S.C. 154(b) by 334 days.

(21) Appl. No.: 13/602,718

(22) Filed: Sep. 4, 2012

(65) Prior Publication Data

US 2013/0066209 A1 Mar. 14, 2013

(30) Foreign Application Priority Data

Sep. 12, 2011 (JP) .................................. 2011-197988

(51) Int. Cl.
*A61B 8/00* (2006.01)

(52) U.S. Cl.
CPC ............. *A61B 8/4494* (2013.01); *A61B 8/4444* (2013.01)

(58) Field of Classification Search
CPC ................................ A61B 8/00; A61B 8/4494
USPC .......................................... 600/407, 437, 459
See application file for complete search history.

(56) References Cited

U.S. PATENT DOCUMENTS

| 7,466,064 B2 | 12/2008 | Sugiura et al. |
| 2011/0221306 A1 | 9/2011 | Matsuda |
| 2011/0252890 A1 | 10/2011 | Matsuda |

FOREIGN PATENT DOCUMENTS

| JP | 10-051041 A | 2/1998 |
| JP | 2006-229901 A | 8/2006 |
| JP | 2011-066197 A | 3/2011 |
| JP | 2011-211164 A | 10/2011 |
| JP | 2011-223490 A | 11/2011 |

*Primary Examiner* — Peter Luong
(74) *Attorney, Agent, or Firm* — Global IP Counselors, LLP (57) ABSTRACT

An ultrasonic probe includes a piezoelectric element including a support body, a lower electrode layer, first and second piezoelectric layers, and an upper electrode layer. The support body has an opening section and a displacement section covering the opening section on one side of the support body. The lower electrode layer is disposed on the one side of the support body and continuously extending from an inside to an outside of the opening section when viewed in a plan view along a thickness direction of the support body. The first piezoelectric layer is disposed on the lower electrode layer and positioned inside of the opening section when viewed in the plan view. The upper electrode layer is disposed on the first piezoelectric layer. The second piezoelectric layer is disposed on the lower electrode layer and positioned outside of the opening section when viewed in the plan view.

20 Claims, 8 Drawing Sheets

ULTRASONIC PROBE AND ULTRASONIC IMAGE DIAGNOSTIC DEVICE

CROSS-REFERENCE TO RELATED APPLICATIONS

This application claims priority to Japanese Patent Application No. 2011-197988 filed on Sep. 12, 2011. The entire disclosure of Japanese Patent Application No. 2011-197988 is hereby incorporated herein by reference.

BACKGROUND

1. Technical Field

The present invention relates to an ultrasonic probe that uses a piezoelectric element comprising a piezoelectric material deposited on a thin film. The present invention also relates to an ultrasonic image diagnostic device equipped with such an ultrasonic probe.

2. Related Art

There is a known conventional piezoelectric element (ultrasonic element) that comprises a piezoelectric material laminated onto a support film and is configured to vibrate the support film and emit an ultrasonic wave when a voltage is applied to the piezoelectric material and causes it to vibrate (e.g., see Japanese Laid-Open Patent Publication No. 2006-229901).

The ultrasonic element disclosed in the above mentioned publication has a piezoelectric oscillator comprising a thin film of piezoelectric material arranged on a membrane and sandwiched between metal films serving as electrodes. With this kind of ultrasonic element, when a voltage is applied across the upper and lower metal electrode film layers, the piezoelectric material film vibrates and causes the membrane on which the piezoelectric material film is formed to vibrate such that an ultrasonic wave is emitted.

SUMMARY

When an ultrasonic element like that presented in the above mentioned publication is manufactured, typically the lower-layer metal electrode film is formed on the membrane and the piezoelectric material film is formed over the metal electrode film. Afterwards, the piezoelectric material film is etched to form a pattern of a prescribed shape. The upper metal electrode layer is formed in a similar fashion. That is, a metal electrode layer is formed over the lower-layer metal electrode film and the piezoelectric material film and this upper metal electrode layer is etched to form a pattern of a prescribed shape.

However, with this method etching is performed repeatedly and the lower metal electrode layer ends up getting etched (over-etching) when the piezoelectric material film and the upper metal electrode layer are etched. Consequently, the film thickness dimension of the lower metal electrode layer decreases. As the thickness dimension of the metal electrode film decreases, the electrical resistance increases. Consequently, when a piezoelectric element manufactured using the conventional technology is used as an ultrasonic probe, the electric power consumption increases and the sound pressure of the ultrasonic wave emitted from the probe decreases. As a result, the probe is difficult to control in a high-frequency region.

The present invention was conceived in view of the problem just explained and its object is to provide an ultrasonic probe that uses a piezoelectric element whose electrodes have a small electrical resistance and an ultrasonic image diagnostic device that uses the ultrasonic probe.

An ultrasonic probe according to one aspect of the present invention includes a piezoelectric element including a support body, a lower electrode layer, first and second piezoelectric layers, and an upper electrode layer. The support body has an opening section and a displacement section covering the opening section on one side of the support body. The lower electrode layer is disposed on the one side of the support body and continuously extending from an inside of the opening section to an outside of the opening section when viewed in a plan view along a thickness direction of the support body. The first piezoelectric layer is disposed on the lower electrode layer and positioned inside of the opening section when viewed in the plan view. The upper electrode layer is disposed on the first piezoelectric layer. The second piezoelectric layer is disposed on the lower electrode layer and positioned outside of the opening section when viewed in the plan view.

According to this aspect of the invention, the first piezoelectric layer and the second piezoelectric layer are laminated over the lower electrode layer. As a result, the lower electrode layer is protected because it is covered by the first piezoelectric layer and the second piezoelectric layer and the lower electrode layer is not over-etched when the piezoelectric layers and the upper electrode layer of the piezoelectric element are formed. Thus, the electrical resistance of the lower electrode layer can be prevented from increasing and a piezoelectric element having a lower electrical resistance can be provided. Since the piezoelectric element has a lower electrical resistance, energy conservation can be promoted because a vibration having a larger amplitude can be obtained with a smaller amount of electric power when a voltage is applied across the lower electrode layer and the upper electrode layer such that a displacement section vibrates. Also, when a displacement amount of the support film is detected based on an electric current value outputted from the first piezoelectric layer, the amount of loss of the current outputted from the first piezoelectric layer can be suppressed because the electrical resistance of the lower electrode wire section is small and, thus, the displacement of the support film can be detected more accurately.

It is feasible to make the thickness dimension of the lower electrode layer larger in anticipation that over-etching of the lower electrode layer will occur as explained previously, but over-etching does not occur at the portions where the piezoelectric layer is formed. Consequently, the thickness dimension of the lower electrode layer will be larger and the total thickness dimension will increase at the portions where the piezoelectric layer and the upper electrode layer are layered over the lower electrode layer. Conversely, with the above aspect of the present invention, the film thickness dimension of the lower electrode layer can be set without taking into account the increased electrical resistance and film thickness variation that results when over-etching of the lower electrode occurs and, thus, the piezoelectric element can be made thinner.

It is also possible for the second piezoelectric layer to be made of the same material as the first piezoelectric layer and, in such a case, the first piezoelectric layer and the second piezoelectric layer can be formed simultaneously. Thus, compared to a technology in which a protective layer for protecting the lower electrode layer is provided separately, the piezoelectric element can be manufactured more simply and the manufacturing cost can be reduced.

Additionally, in an ultrasonic probe according to another aspect of the present invention, the second piezoelectric layer is preferably disposed at a position that does not overlap the opening section in the plan view.

When the support film covering the opening section is to be displaced in coordination with a vibration of the first piezoelectric layer or when the support film is to be displaced due to a stress resulting from an external influence, the displacement amount of the displacement section where the support film undergoes displacement can be increased by configuring the displacement section such that an edge portion of the displacement section has a smaller film thickness dimension. With this aspect of the present invention, since the second piezoelectric layer is provided at such a position that it does not overlap with the edge portion of the displacement section, the second piezoelectric layer does not increase the thickness dimension near the edge portion of the displacement section. Thus, a large displacement amount can be achieved regardless of whether the displacement section will be displaced by vibration of the first piezoelectric layer or by an external influence. For example, when an ultrasonic wave is generated by vibrating the displacement section, the displacement section can be vibrated with a larger amplitude using less electric power and an ultrasonic wave having a larger sound pressure can be produced than with a piezoelectric element in which the second piezoelectric layer is layered over the edge of the displacement section. Meanwhile, when an ultrasonic wave is to be received, the received ultrasonic wave can cause a larger vibration of the displacement section. As a result, the reception sensitivity can be increased and the ultrasonic wave can be detected more accurately.

An ultrasonic probe according to another aspect of the present invention may further include a wiring layer disposed on the second piezoelectric layer and connected to the lower electrode layer.

In this aspect of the present invention, the wiring layer and the lower electrode layer can be separated by forming the wiring layer on the piezoelectric layer. When a plurality of wiring patterns are formed on a single flat substrate, the line width of the wiring patterns is limited by size of the substrate and there is a possibility that the electrical resistance will increase. With the above aspect of the present invention, however, since a wiring layer is formed on the second piezoelectric layer, the wiring patterns can be formed at two levels, i.e., on the substrate and on the second piezoelectric layer. As a result, compared to a piezoelectric element in which a plurality of wiring patterns are formed on one substrate, a smaller sized substrate can be used and an increase of electrical resistance can be prevented.

An ultrasonic probe according to another aspect of the present invention may further include a wiring layer disposed on the second piezoelectric layer and connected to the upper electrode layer.

With this aspect of the present invention, the upper electrode wire section and the lower electrode wire section can be arranged to cross each other without forming a separate insulation layer. As a result, the degree of freedom regarding the wiring pattern is increased and an increase of the electrical resistance can be prevented.

In an ultrasonic probe according to another aspect of the present invention, the lower electrode layer preferably has a lower electrode main body section, on which the first piezoelectric layer is disposed, and a lower electrode wire section continuously extending from the lower electrode main body section to the outside of the opening section when viewed in the plan view. Moreover, the lower electrode wire section preferably includes an element connecting wire connected to the lower electrode main body section and continuously extending between the inside of the opening section and the outside of the opening section, and a lower electrode wire extending from the element connecting wire and positioned outside of the opening section when viewed in the plain view, the lower electrode wire having a narrower line width than a line width of the element connecting wire. Furthermore, the second piezoelectric layer is preferably disposed over the lower electrode wire of the lower electrode wire section.

With this aspect of the invention, the second piezoelectric layer covers the narrower lower electrode wire portion of the lower electrode wire section. Since the electrical resistance of the lower electrode wire section decreases as the line width dimension increases, it is preferable for the line width of the lower electrode wire section to be larger. However, when a piezoelectric element is actually arranged on a substrate, there are cases in which sufficient space cannot be secured and the line width of the lower electrode wire must be made narrower than the element connecting wire due to the relationship with respect to other elements and the wiring patterns of those elements. In such a case, the resistance of the lower electrode wire will become large if the lower electrode wire is over-etched when the piezoelectric layers and the upper electrode are patterned. However, in the above aspect of the present invention, the second piezoelectric layer is layered over the lower electrode wire with the narrower line width. Consequently, when the piezoelectric layer and the upper electrode are patterned, the lower electrode wire is not over-etched and the electrical resistance can be prevented from increasing.

In an ultrasonic probe according to another aspect of the present invention, a plurality of the piezoelectric elements are preferably arranged at a constant pitch along a first direction and at a constant pitch along a second direction perpendicular to the first direction.

With this aspect of the invention, the ultrasonic probe is provided with a plurality of piezoelectric elements arranged along two directions so as to form an array. Since a portion of the lower electrode layer is covered by the second piezoelectric layer in each of the piezoelectric elements, increased electrical resistance caused by over-etching can be suppressed. Consequently, in a case where the support film will be vibrated in order to emit an ultrasonic wave, an ultrasonic wave having a large sound pressure (large amplitude) can be produced with a small electric power consumption. Meanwhile, in a case where an ultrasonic signal will be detected by receiving the ultrasonic wave with the support film, a larger electric signal (larger current value) can be outputted and the detection accuracy can be improved.

With this kind of ultrasonic probe, it is necessary for a lower electrode wire section to be connected to each of the piezoelectric elements and the line width of the lower electrode wire sections will be restricted to a smaller size if the size of the ultrasonic probe is reduced. In such a case, the electrical resistance of the lower electrode wire sections will increase. If the second piezoelectric layer is not formed on top of these lower electrode wire sections, then the electrode resistance could possibly increase even further due to over-etching of the lower electrode wire sections. With the above aspect of the present invention, however, the second piezoelectric layer is formed on the lower electrode wire section even if the line width of the lower electrode wire section is small. As a result, the resistance can be prevented from increasing when the piezoelectric layers and the upper electrode layer are patterned.

In an ultrasonic probe according to another aspect of the present invention, the pitch at which the piezoelectric elements are arranged along the first direction and the pitch at which the piezoelectric elements are arranged along the second direction are preferably the same. With this aspect of the invention, when an image of a test object is acquired with the ultrasonic probe, an undistorted image can be obtained because the pitch in the first direction and the pitch in the second direction are the same.

An ultrasonic image diagnostic device according to another aspect of the present invention includes the ultrasonic probe as explained heretofore.

With this aspect of the invention, the total electric power consumption of the ultrasonic image diagnostic device can be suppressed because, as explained previously, the piezoelectric elements used in the ultrasonic probe have a small electrical resistance. The ultrasonic image diagnostic device also can enjoy various other performance improvements resulting from using an ultrasonic probe according to the present invention. For example, a highly accurate image can be acquired because the displacement of the support film can be detected with a high degree of accuracy.

BRIEF DESCRIPTION OF THE DRAWINGS

Referring now to the attached drawings which form a part of this original disclosure.

DETAILED DESCRIPTION OF EXEMPLARY EMBODIMENTS

First Embodiment

A piezoelectric element according to a first embodiment used in an ultrasonic probe according to the present invention will now be explained based on the drawings.

Piezoelectric Element

Figure 1:
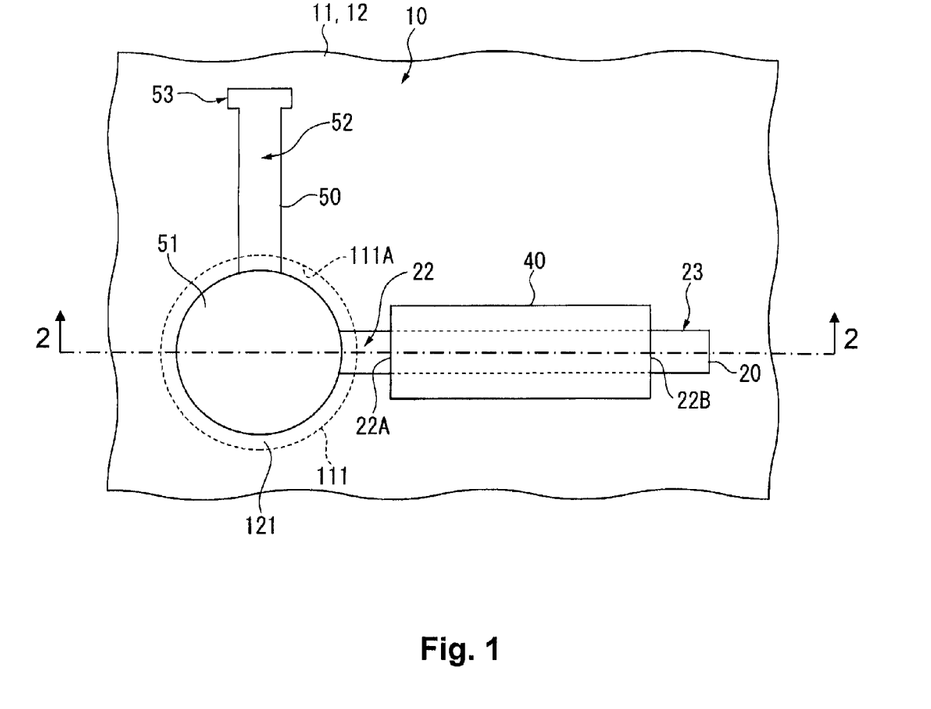
FIG. 1 is a plan view of a piezoelectric element according to a first embodiment of the present invention.
Figure 2:
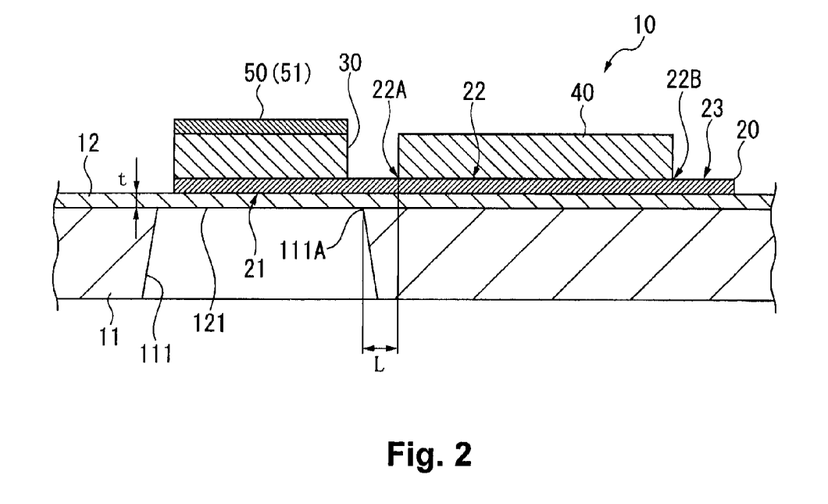
FIG. 2 is a sectional view of the piezoelectric element according to the first embodiment taken along a section line 2-2 in FIG. 1.

FIG. 1 is a plan view of the piezoelectric element according to the first embodiment. FIG. 2 is a sectional view of the piezoelectric element according to the first embodiment taken along a section line 2-2 in FIG. 1. As shown in FIG. 1, the piezoelectric element 10 comprises a substrate 11 having an opening section 111 formed therein, a support film 12 formed on the substrate 11 so as to straddle across the inside and outside of the opening section 111, a lower electrode layer 20 formed on the support film 12, a first piezoelectric layer 30 formed within the opening section 111 when viewed in the plan view, a second piezoelectric layer 40 formed outside the opening section 111, and an upper electrode layer 50 formed such that it straddles across the inside and outside of the opening section 111. The substrate 11 and the support film 12 constitute a support body, and the portion of the support film 12 in a region blocking the opening section 111 is called a membrane 121 and forms a displacement section of this embodiment.

This embodiment exemplifies a case in which the support body is made by forming a support film 12 on a substrate 11 having a through hole serving an opening section 111 formed therein, thereby obtaining a membrane 121 serving as a displacement section. However, the invention is not limited to this configuration and, for example, it is acceptable for the opening section 111 to have the form of a recessed groove and for the support film 12 to be arranged to block the opening of the groove-like opening section 111. It is also acceptable to form a recessed groove in the substrate 11 and let a bottom portion of the recessed groove serve as the displacement section of the support body.

Also, although this embodiment presents an example in which the substrate 11 and the support film 12 form the support body, it is acceptable, for example, to adopt a configuration in which an insulating film or other layer is formed on top of the support film 12 and the lower electrode layer 20 is formed on this other layer.

The piezoelectric element 10 can be used, for example, as an ultrasonic wave transmitting element that outputs an ultrasonic wave when a voltage is applied to the first piezoelectric layer 30 and causes the support film 12 to vibrate, as an ultrasonic wave receiving element in which the support film 12 receives an ultrasonic wave and the first piezoelectric layer 30 outputs an electric signal corresponding to the vibration, as a stress detecting element that detects a stress occurring in the support film 12 based on an electric signal outputted from the first piezoelectric layer 30, or as a drive force generating element that operates by driving the first piezoelectric element 30 and touching the support film 12 against an object so as to impart a drive force to the object. In this embodiment, the invention will be explained using a piezoelectric element 10 that function as an ultrasonic wave generating element as an example.

The substrate 11 is made of a semiconductor forming material, e.g., silicon (Si) that can easily accommodate etching and other processes. The opening section 111 formed in the substrate 11 preferably has a circular shape in a plan view. Thus, the stresses resulting from deflection of the membrane 121, i.e., the portion of the support film 12 located inside the opening section 111, can be made more uniform. If, for example, the opening section 111 were made to be rectangular, then even if the first piezoelectric layer 30 were formed in a center portion of the rectangular shape and only positions at an equal distance from a center point of the membrane 121 were considered, there would be regions where the support film 12 deflects more readily and regions where the support film 12 deflects less readily. Conversely, if the opening section 111 is made to be circular as in this embodiment, then the distance from the center of the membrane to an edge 111A will be equal at all positions along the edge 111A. Consequently, the support film 12 will deflect with the same degree of readiness at all positions located an equal distance from the center point of the membrane 121 and the membrane 121 can be made to deflect in a uniform fashion.

The support film 12 is formed on the substrate 11 such that it blocks the opening section 111. The support membrane has, for example, a two-layer structure comprising an SiO$_2$ film and a ZrO$_2$ layer. In such a case, if the substrate 11 is a silicon substrate, the SiO$_2$ layer can be formed on the substrate surface by a thermal oxidation process. Meanwhile, the ZrO$_2$ layer is formed on the SiO$_2$ layer by sputtering or another method. If, for example, PZT is used for the first piezoelectric layer 30 or the second piezoelectric layer 40 the ZrO$_2$ layer, then the ZrO$_2$ layer serves as a layer for preventing diffusion of the lead (Pb) in the PZT into the SiO$_2$ layer. The ZrO$_2$ layer also serves to improve a deflection efficiency with respect to deformation of a piezoelectric layer 131.

The lower electrode layer 20 comprises a lower electrode main body section 21, a lower electrode wire section 22, and a lower electrode terminal section 23. The lower electrode main body section 21 is formed such that it lies inside the opening section 111 in a plan view and has the first piezoelectric layer 30 formed thereon. The lower electrode wire section 22 is connected to the lower electrode main body section 21, formed such that it straddles the inside and outside of the opening section 111, and does not have the first piezoelectric element 30 formed thereon. The lower electrode terminal section 23 is formed on a tip end portion of the lower electrode wire section 22.

The first piezoelectric layer 30 is formed on the lower electrode main body section 21 of the lower electrode layer 20. The first piezoelectric layer 30 is made of, for example, PZT (lead zirconate titanate) and formed as a film. In this embodiment, although PZT is used as the material of the first piezoelectric layer 30, it is acceptable to use any other material that can undergo contraction in an in-plane direction when a voltage is applied, e.g., lead titanium oxide (PbTiO3), laid zirconium oxide (PbZrO3), lead-lanthanum titanium oxide ((Pb, La)Tio3). The first piezoelectric element 30 elongates and contracts in an in-plane direction when a voltage is applied to the lower electrode main body section 21 and the upper electrode layer 50 (explained later). One side of the first piezoelectric layer 30 is joined to the support film 12 through the lower electrode main body section 21 and the other side has the upper electrode layer 50 formed thereon. However, since there are no other layers formed over the upper electrode layer 50, it is more difficult for the support film 12 side of the first piezoelectric layer 30 to elongate and contract and easier for the upper electrode layer 50 side to elongate and contract. When a voltage is applied to the first piezoelectric layer 30, the first piezoelectric layer 30 deflects so that it is convex toward the opening section 111 and causes the membrane 121 to deflect. Thus, by applying an alternating current to the first piezoelectric element 30, it is possible to vibrate the membrane 121 in a film thickness direction and use the vibration of the membrane 121 to emit an ultrasonic wave from the opening section 111.

In the plan view as shown in FIG. 1, a portion of the upper electrode layer 50 is layered over the first piezoelectric layer 30 and arranged in such a position that it is insulated from the lower electrode layer 20. More specifically, the upper electrode layer 50 comprises an upper electrode main body section, an upper electrode wire section 52, and an upper electrode terminal section 53. The upper electrode main body section 51 is layered over the first piezoelectric layer 30. The upper electrode wire section 52 is connected to the upper electrode main body section 51 and formed such that it extends in a different direction than the lower electrode wire section 22 and straddles the inside and outside of the opening section 111 in a plan view. The upper electrode terminal section 53 is formed on a tip end portion of the upper electrode wire section 52. The region of the first piezoelectric layer 30 where the upper electrode layer 50 and the lower electrode main body section 21 overlap each other is a region where the first piezoelectric layer 30 contracts when a voltage is applied.

The second piezoelectric layer 40 is made of PZT, the same material that the first piezoelectric layer 30 is made of. The second piezoelectric layer 40 is formed on the support film 12 in a region outside the opening section 111 and arranged to cover the lower electrode wire section 22 of the lower electrode layer 20. More specifically, the second piezoelectric layer 40 is formed on the lower electrode wire section 22 and configured to cover a region between an end position 22A and a connecting section 22b. The end portion 22A is separated from the edge 111A of the opening section 111 under the support film 12 by a prescribed distance where the second piezoelectric layer 40 will not affect the deflection of the membrane 121. The connecting section 22b is where the lower electrode wire section 22 connects to the lower electrode terminal section 23. This arrangement is adopted because if the second piezoelectric layer 40 were formed so as to overlap the edge 111A of the opening section 111, then the rigidity of membrane 121 would increase such that the membrane 121 is more resistant to deflection and the sound pressure of the ultrasonic waves produced would be smaller. It is more preferable for the second piezoelectric element 40 to be formed on the lower electrode wire section 22 so as to span from the end position 22A to the connecting portion 22B, where the end position 22a is located at a distance L from the edge 111A of the opening section 111 and the distance L satisfies the equation (1) shown below. In the equation, t is the thickness dimension of the support film 12.

Equation (1)

$$L > 5t \quad (1)$$

When the membrane 121 of the support film 12 deflects, a moment acts on the support film 12 in such a direction as to pull the support film 12 toward the opening section 111A. The moment causes a tensile force to act on the portion of the support film 12 within a distance of 5t from the edge 111A of the opening section 111 in a plan view. Thus, forming the second piezoelectric layer 40 within this distance would create a resistance to deflection of the membrane 121 and cause the sound pressure of the ultrasonic waves to decrease. Conversely, by forming the second piezoelectric layer 40 at a distance of 5t or larger from the edge 111A of the opening section 111 in a plan view, the aforementioned resistance to deflection will not affect the membrane 121 and the membrane 121 can deflect well. Conversely, if the end portion of the second piezoelectric layer 40 is positioned too far from the opening section 111, then the exposed surface area of the lower electrode wire section 22 will be large and there will be a possibility that the exposed portion of the lower electrode wire section 22 will be over-etched and the electrical resistance will increase when the first and second piezoelectric layers 30 and 40 and the upper electrode layer 50 are patterned. It is preferred for the second piezoelectric layer 40 to be formed such that it covers a region spanning from a position located 5t from the edge 111A of the opening section 111 to a position corresponding to the connecting portion 22B where the lower electrode wire section 22 connects to the lower electrode terminal section 23. In such a case, the second piezoelectric layer 40 is not formed on the lower electrode terminal section 23 because a wire for applying a voltage to the first piezoelectric layer 30 is connected to the lower electrode terminal section 23.

Manufacturing Method of Piezoelectric Element

Figure 3A:
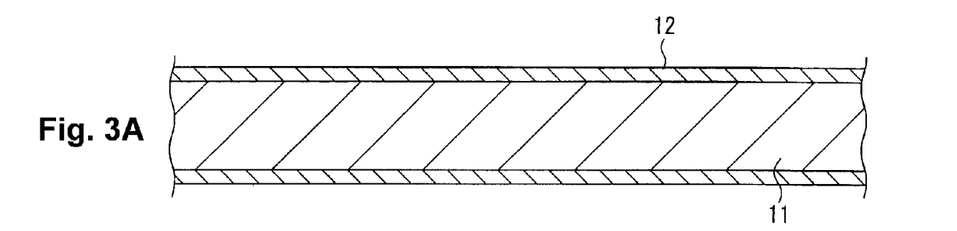
FIGS. 3A to 3D are a series of sectional views showing a portion of a method for manufacturing the piezoelectric element.

A method of manufacturing the piezoelectric element explained heretofore will now be explained based on the drawings. FIG. 3 and FIG. 4 are sectional views showing manufacturing steps for manufacturing the piezoelectric element. In order to manufacture the piezoelectric element 10, first a heat treatment is applied to the substrate 11 (Si) and a layer of SiO2 is formed on the surface of the substrate 11 as shown in FIG. 3A. Additionally, Zr layer is deposited onto the SiO2 layer by sputtering and the Zr layer is oxidized to form a ZrO2 layer. In this way, a support film 12 having a thickness of, for example, 3 μm is formed.

Figure 3B:
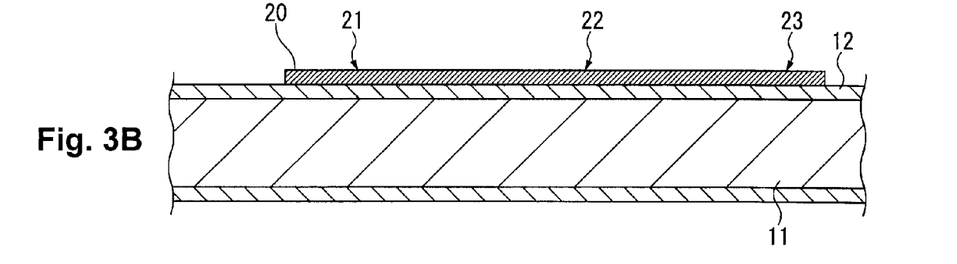

Afterwards, the lower electrode layer 20 is formed on one side of the substrate by, for example, sputtering. There are no particular limitations on the material of the lower electrode layer 20 so long as it forms a conductive film. In this embodiment, the lower electrode layer 20 has a layered structure of Ti/Ir/Pt/Ti and is formed uniformly such that it has a thickness dimension of, for example, 0.2 μm after the piezoelectric layers are baked. Next, photoresist is deposited onto the lower electrode layer 20 where the lower electrode main body section 21 and the lower electrode wire section 22 will be formed using photolithography, for example. Next, the portions of the lower electrode layer where photoresist was not deposited are removed by etching to pattern the lower electrode layer and the lower electrode main body section 21, the lower electrode wire section 22, and the lower electrode terminal section 23 are formed as shown in FIG. 3B (lower electrode patterning step).

Figure 3C:
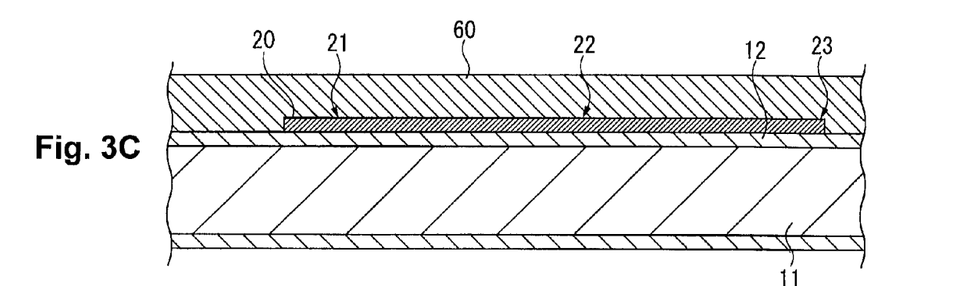
Figure 3D:
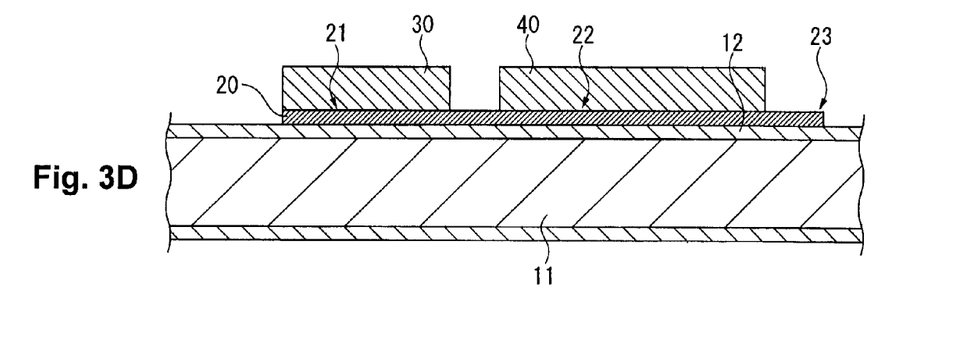

Afterwards, as shown in FIG. 3C, a piezoelectric layer 60 made of PZT is formed on the aforementioned one side of the substrate 11 where the lower electrode layer 20 has been patterned. The piezoelectric layer 60 is formed on the layer 12 using a metal organic decomposition (MOD) method to a total thickness dimension of, for example, 1.4 μm (piezoelectric layer lamination step). Then, photoresist is deposited onto the piezoelectric layer 60 in positions where the first piezoelectric layer 30 and the second piezoelectric layer 40 will be formed using, for example, photolithography and the regions where the photoresist was not deposited are removed by etching. In this way, the first piezoelectric layer 30 is formed on the lower electrode main body section 21 and the second piezoelectric layer 40 is formed on the lower electrode wire section 22 as shown in FIG. 3D (piezoelectric layer patterning step). With this piezoelectric material patterning step, the lower electrode layer 20 is not etched in the regions where the first piezoelectric layer 30 and the second piezoelectric layer 40 are formed and, thus, such disadvantages as increased electrical resistance do not occur.

Although there are cases in which the piezoelectric layer 60 will be over-etched in a region of the lower electrode wire section 22 where the first piezoelectric layer 30 is not provided over the opening section 111 and in a region of the lower electrode wire section 22 lying within a distance L, i.e., 5t (in this embodiment, t=3 μm and, thus, L=15 μm) from the edge 111A of the opening section 111, these regions occupy only a small portion of the entire lower electrode wire section 22 and there will be little effect even if the electrical resistance rises in these regions.

Figure 4A:
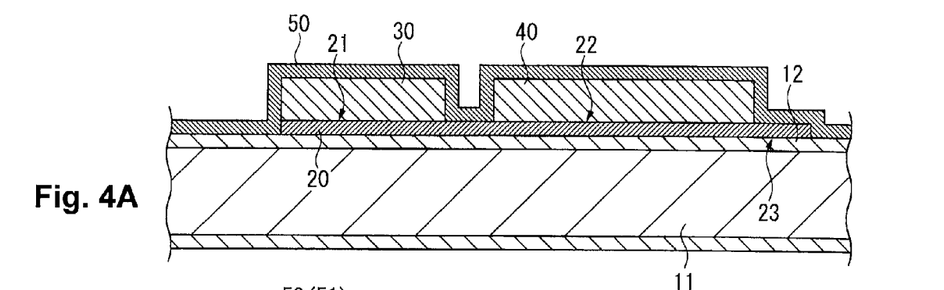
FIGS. 4A to 4D are a series of sectional views showing the remaining portion of a method for manufacturing the piezoelectric element.
Figure 4B:
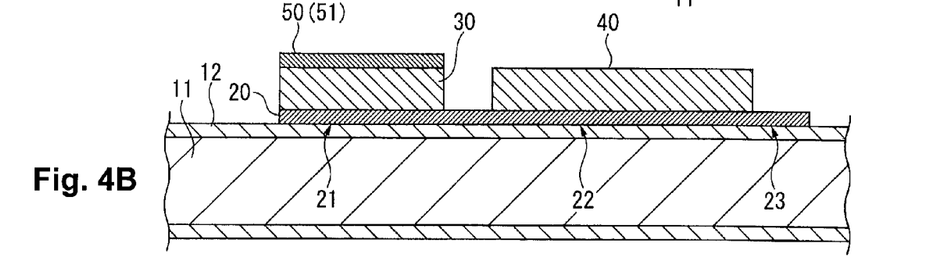

Afterwards, as shown in FIG. 4A, the upper electrode layer 50 is deposited uniformly onto the aforementioned one side of the substrate 11 by, for example, sputtering. Similarly to the lower electrode layer 20, there are no particular limitations on the material of the upper electrode layer 50 so long as it forms a conductive film. In this embodiment, the upper electrode layer 50 is an Ir film having a thickness dimension of, for example, 50 nm (upper electrode layer laminating step). Then, photoresist for patterning the upper electrode main body section 51 and the upper electrode wire section 52, and the upper electrode terminal section 53 using, for example, a photolithography method, is deposited onto the upper electrode layer 50, and the regions where the photoresist was not deposited are removed by etching. In this way, the upper electrode layer 50 is patterned as shown in FIG. 4B (upper electrode patterning step). Similarly to the previously explained piezoelectric layer patterning step, over-etching of the lower electrode layer 20 is prevented in the upper electrode patterning step because the lower electrode layer 20 is covered by the first piezoelectric layer 30 and the second piezoelectric layer 40. As a result, the electrical resistance of the lower electrode layer 20 can be prevented from increasing.

Figure 4C:
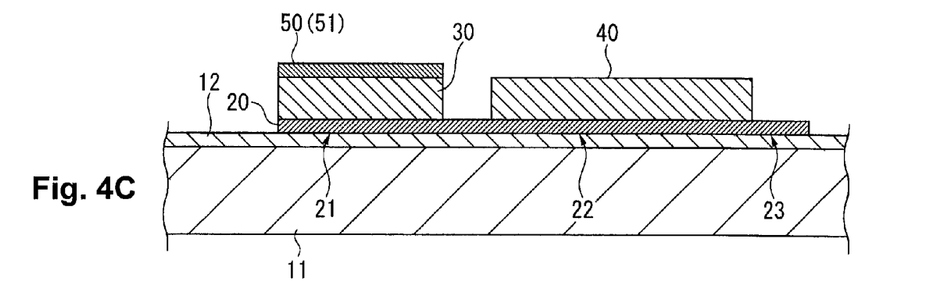

Next, the thickness dimension of the substrate 11 is adjusted. As shown in FIG. 4C, this adjustment is accomplished by, for example, cutting or grinding the other side of the substrate 11 (the side from which the ultrasonic waves are emitted), i.e., the opposite side as the side on which the lower electrode layer 20, the first piezoelectric layer 30, the second piezoelectric layer 40, and the upper electrode layer 50 are formed. By executing this cutting or grinding process, the amount of etching required when the opening section 111 is formed can be reduced. The opening section 111 is preferably formed by reactive ion etching (RIE) using an inductive coupled plasma (ICP) etching device, and the substrate 11 is preferably cut or ground to a thickness dimension of 200 μm while taking into consideration the depth dimension that will be reached by etching, the rigidity required to resist warping of the substrate caused by film stresses, and strength of the substrate with respect to handling.

Figure 4D:
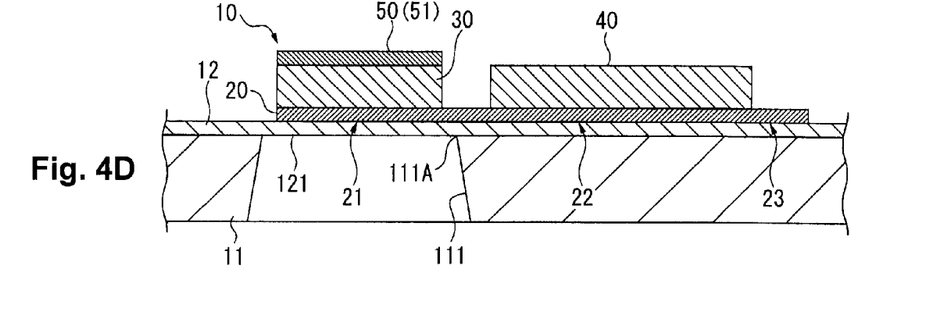

In order to form the opening section 111, photoresist is deposited onto the other side of the substrate 11 except where the opening section 111 is to be formed. The photoresist is applied to a thickness of for example, approximately 10 μm to resist etching of the substrate 11. Afterwards, as shown in FIG. 4D, the ICP etching device is used to etch the substrate 11 from the aforementioned other side to the $SiO_2$ layer of the support film 12.

This etching completes the fabrication of the piezoelectric element 10.

Operational Effects of First Embodiment

In a piezoelectric element according to the first embodiment, the lower electrode layer 20 straddles across the inside and outside of the opening section 111. The first piezoelectric layer 30 is formed on the lower electrode main body section 21, which is a portion of the lower electrode layer 20 formed inside the opening section 111. The second piezoelectric layer 40 is formed on a portion of the lower electrode wire section 22 that lies outside the opening section 111. Consequently, when the piezoelectric layer 60 is etched to form the first piezoelectric layer 30 and the second piezoelectric layer 40, over-etching of the lower electrode layer can be prevented such that a disadvantageous increase of the electrical resistance does not occur. Consequently, the amount of elongation and contraction of the first piezoelectric layer 30 can be increased with low electric power and an ultrasonic wave having a large sound pressure can be generated by the vibration of the membrane 121. With this embodiment, the thickness dimension of the lower electrode layer 20 can be decreased because it is not necessary to increase the thickness dimension of the lower electrode layer 20 in anticipation of over-etching. As a result, the piezoelectric element 10 as a whole can be made thinner.

In the first embodiment, the first piezoelectric layer 30 and second piezoelectric layer 40 are made of the same material, PZT. Consequently, the first piezoelectric layer 30 and the second piezoelectric layer 40 can be formed simultaneously with the piezoelectric layer lamination step and the piezoelectric layer patterning step. As a result, both the manufacturing process and the structure of the piezoelectric element can be simplified in comparison with a process in which a separate protective layer is formed on the lower electrode layer 20.

The second piezoelectric layer 40 is formed in a position that does not overlap the edge 111A of the opening section 111 in a plan view. Consequently, since second piezoelectric layer 40 does not impose a resistance to deflection the membrane 121, the membrane 121 can be made to vibrate with a larger amplitude than in a case in which the second piezoelectric layer 40 is formed over the edge 111A of the opening section 111. As a result, an ultrasonic wave having a large sound pressure can be generated even if the voltage applied to the first piezoelectric layer 30 is a low voltage.

The second piezoelectric layer 40 is formed on a portion of the lower electrode wire section 22 that spans from an end position 22A located at a distance L from the edge 111A of the opening section 111 to a connecting portion 22B where the lower electrode wire section 22 connects to the lower electrode terminal section 23, where the distance L equals 5 times the thickness dimension of the support film 12. When the membrane 121 deflects, a moment acts on the support film 12 in a direction of entering the opening section 111 and the moment causes a tensile force to act on a portion of the support film 12 near the edge 111A of the opening section 111 such that the support film 12 is pulled toward the opening section 111 when the support film 12 elongates and contracts. If the second piezoelectric layer 40 were formed near the edge of the opening section 111, then the elongation and contraction of the support film 12 would be restricted and the deflection amount of the membrane 121 could possibly be limited. Conversely, in the first embodiment, the second piezoelectric element 40 is formed in a position separated from the edge 111A of the opening section 111 by a distance L such that the resistance to deflection of the membrane 121 is not increased and the deflection amount of the membrane 121 does not decrease. As a result, it is possible to produce an ultrasonic wave having a larger sound pressure than can be produced with a piezoelectric element in which the distance from the edge 111A of the opening section 111 to the position where the second piezoelectric layer 40 is formed is smaller than the distance L.

Second Embodiment

Figure 5:
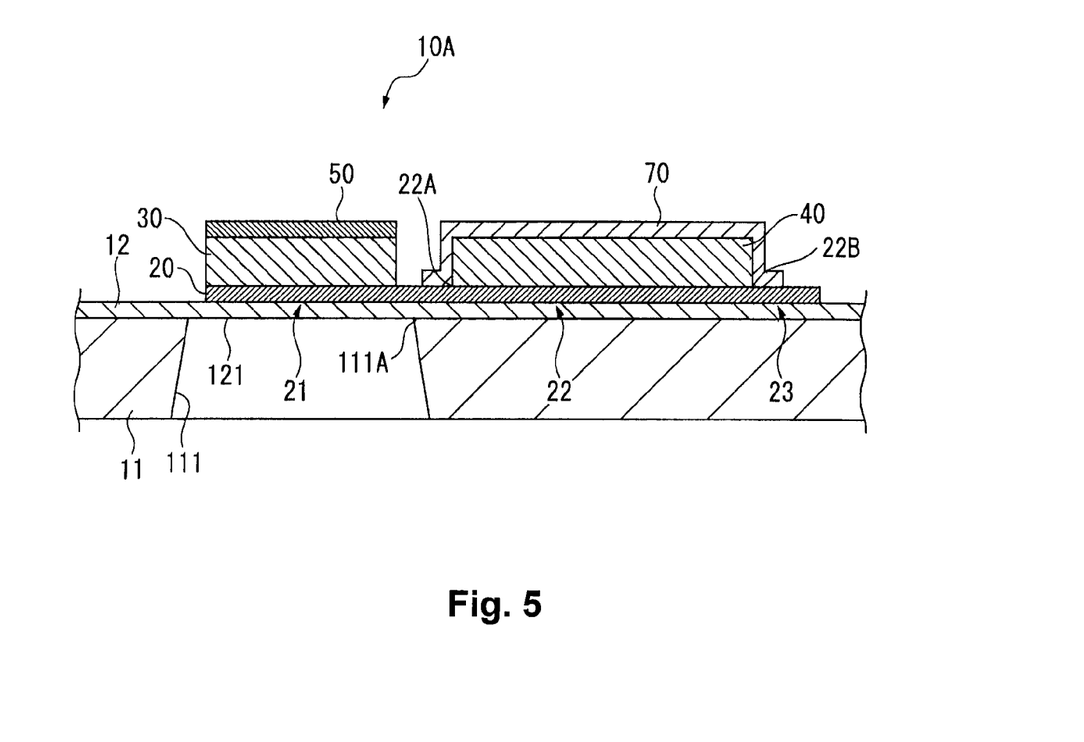
FIG. 5 is a sectional view of a piezoelectric element according to a second embodiment of the present invention.

A piezoelectric element according to a second embodiment of the present invention will now be explained based on the drawings. FIG. 5 is a sectional view of the piezoelectric element according to the second embodiment used in an ultrasonic probe. The piezoelectric element 10A according to the second embodiment has an auxiliary electrode layer 70 serving as a wiring layer formed on the second piezoelectric layer 40 of the piezoelectric element 10 according to the first embodiment. More specifically, auxiliary electrode layer 70 is formed such that that it connects to the lower electrode layer 20 at the connecting portion 22B, spans over the second piezoelectric electric layer 40, and connects to the lower electrode layer 20 again at the end position 22A of the second piezoelectric layer 40.

This auxiliary electrode layer 70 is made of the same material as the upper electrode layer 50 and is formed simultaneously with the upper electrode layer 50 in the upper electrode patterning step. That is, after the conductive film is formed in the upper electrode lamination step as shown in FIG. 4A, photoresist is applied to the positions where the upper electrode layer 50 and the auxiliary electrode layer 70 will be formed in the upper electrode patterning step. The portions of the conductive film where the photoresist was not applied are then removed by etching so as to form the auxiliary electrode layer 70 as shown in FIG. 5.

Operational Effects of Second Embodiment

The operational effects obtained with the piezoelectric element 10A according to the second embodiment are the same as those obtained with the piezoelectric element 10 according to the first embodiment; the electrical resistance of the lower electrode layer 20 can be prevented from increasing and the piezoelectric element 10A as a whole can be made thinner. Additionally, with the addition of the auxiliary electrode layer 70, the electrical resistance can be reduced further in the wiring portion spanning from the lower electrode terminal section 23 to the lower electrode main body section 21 and the first piezoelectric layer 30 can be driven and made to produce an ultrasonic wave using even less electric power.

Although in the piezoelectric element 10A shown in FIG. 5 an end portion of the auxiliary electrode layer 70 is positioned outside of the edge 111A of the opening section 111, the invention is not limited to such an arrangement and it is acceptable for the auxiliary electrode layer 70 to be configured, for example, to extend along the lower electrode wire section 22 from the end position 22A of the second piezoelectric layer 40 to the first piezoelectric layer 30. The upper electrode layer 50 is formed to a thickness dimension of, for example, 50 nm, and is considerably thinner than the second piezoelectric layer 40. The auxiliary electrode layer 70 is formed at the same time as the upper electrode layer 50 and has the same thickness dimension as the upper electrode layer 50. Thus, even if the auxiliary electrode layer 70 were formed to straddle the inside and the outside of the opening section 111, its effect on the deflection of the membrane would be negligibly small and it would not cause the sound pressure of the ultrasonic waves to decrease. Thus, when the auxiliary electrode layer 70 is formed on the lower electrode wire section 22 such that the auxiliary electrode layer 70 extends from the end position 22A of the second piezoelectric layer 40 to the first piezoelectric layer 30, the auxiliary electrode layer 70 can suppress an increase of electrical resistance that might occur if the portion of the lower electrode wire section 22 spanning from the end position 22A of the second piezoelectric layer 40 to the first piezoelectric layer 30 is over-etched during the piezoelectric layer patterning step and the upper electrode patterning step. As a result, the electrical resistance can be effectively prevented from increasing and an ultrasonic wave having a large sound pressure can be produced with a low voltage. Similarly, it is acceptable for the auxiliary electrode layer 70 to be formed on the lower electrode terminal section 23. In such a case, the auxiliary electrode layer 70 will enable the electrical resistance of the lower electrode terminal section 23 to be prevented from increasing.

Third Embodiment

Figure 6A:
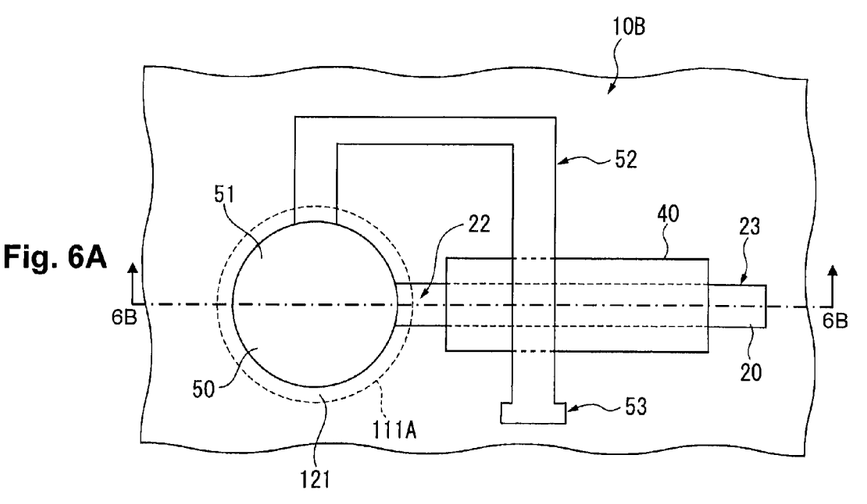
FIG. 6A is a plan view of a piezoelectric element and FIG. 6B is a sectional view of the piezoelectric element taken along a section line 6B-6B in FIG. 6A according to a third embodiment of the present invention.
Figure 6B:
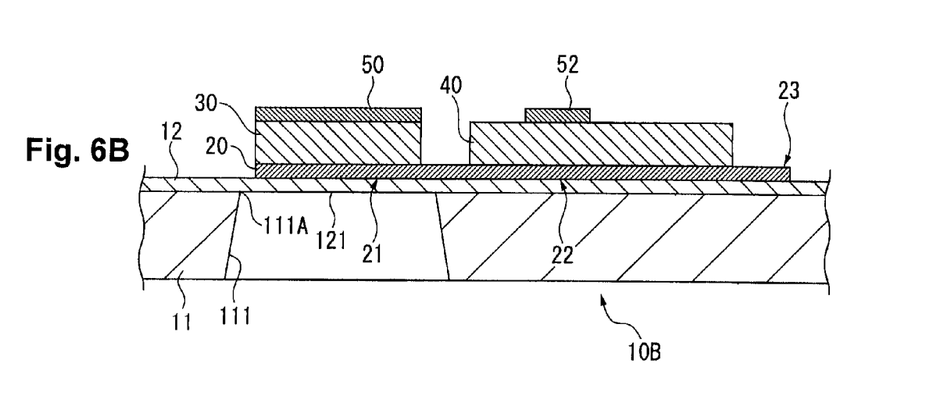

A piezoelectric element used in an ultrasonic probe according to a third embodiment of the present invention will now be explained based on the drawings. FIG. 6A is a plan view of a piezoelectric element and FIG. 6B is a sectional view of the piezoelectric element taken along a section line 6B-6B in FIG. 6A according to the third embodiment. In the piezoelectric element 10A according to the second embodiment, the auxiliary electrode layer 70 is provided over the second piezoelectric layer 40 and connected to the lower electrode layer 20. In the piezoelectric element 10B according to the third embodiment, instead, an upper electrode wire section 52 is formed over the second piezoelectric layer 40.

With the piezoelectric element 10B according to the third embodiment, since the second piezoelectric layer 40 functions as an insulation layer, the structure is simpler and a wiring pattern in which the lower electrode layer 20 and the upper electrode layer 50 cross each other can be formed.

That is, when the piezoelectric elements 10B will be arranged, for example, in an array format, the lower electrode wire section 22 and the upper electrode wire section 52 may be formed so as to cross each other in order to accommodate the elements on 10B an array substrate. In such a case, a separate insulation layer has conventionally been necessary to prevent contact between the upper electrode wire section 22 and the lower electrode wire section 52. With the piezoelectric element 10B according to the third embodiment, since the upper electrode wire section 52 is formed on the second piezoelectric layer 40, the upper electrode wire section 52 and the lower electrode wire section 22 can be crossed without forming a separate insulation layer.

Fourth Embodiment

Figure 7:
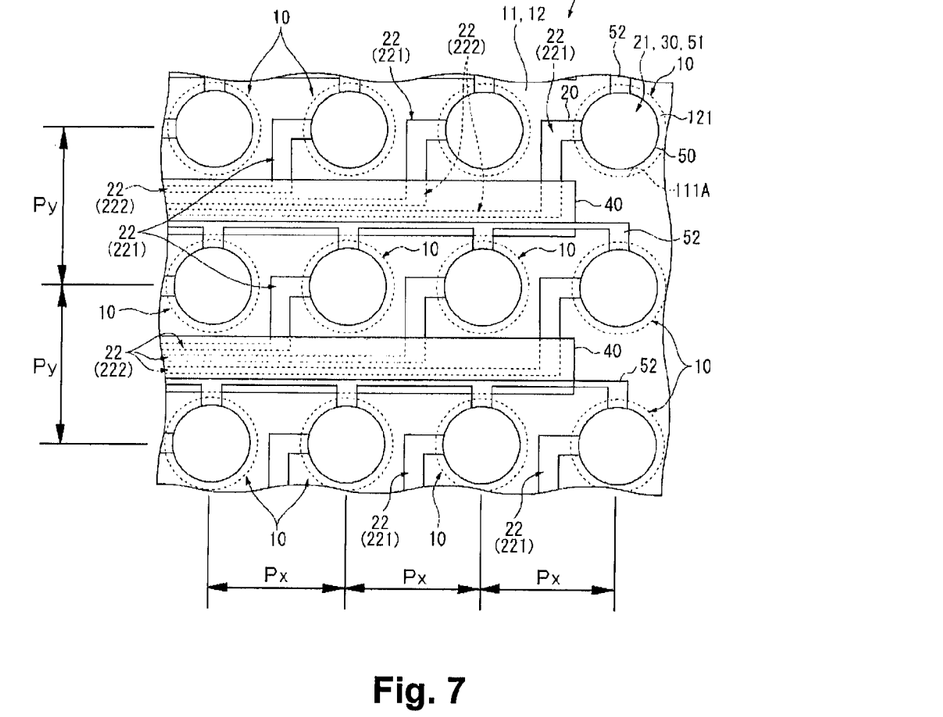
FIG. 7 is a plan view showing a portion of an ultrasonic transducer according to a fourth embodiment of the present invention.

A fourth embodiment used in an ultrasonic probe according to the present invention will now be explained based on the drawings. The fourth embodiment is an ultrasonic transducer in which piezoelectric elements according to the embodiments explained heretofore are arranged. FIG. 7 is a plan view showing a portion of an ultrasonic transducer according to the fourth embodiment. In FIG. 7, the ultrasound transducer 1 has an array structure made up of a plurality of piezoelectric elements 10 according to the first embodiment arranged in a grid form. The array structure enables an echo image of a test object to be acquired. This kind of ultrasonic transducer 1 can concentrate the ultrasonic waves on a desired point if the output timing of the ultrasonic waves are controlled at the piezoelectric elements 10. Although this embodiment exemplifies a case in which the piezoelectric elements 10 arranged on the substrate 11 form an ultrasonic transmitter array for transmitting ultrasound, it is acceptable for the piezoelectric elements 10 to function as ultrasonic receiver elements. It is also acceptable to configure the transducer such that, for example, half of the piezoelectric elements 10 arranged in the grid function as ultrasonic wave transmitter elements and the remaining half function as ultrasonic wave receiver elements. It is also possible to use all of the piezoelectric elements 10 for both transmitting and receiving ultrasonic waves. More specifically, one piezoelectric element 10 can be used as an ultrasonic wave emitting element to emit an ultrasonic wave toward a test object and, afterwards, as an ultrasonic wave receiving element to receive an ultrasonic wave (echo) reflected from the test object. Similarly, by using all of the piezoelectric elements 10 as both ultrasonic wave transmitters and ultrasonic wave receivers, a reflected wave can be received with a high resolution and a high-resolution echo image can be acquired.

With such an ultrasonic transducer 1, an independent lower electrode wire section 22 is provided for each of the piezoelectric elements so that the ultrasonic waves can be concentrated on a desired position by varying the emission timing of ultrasonic waves emitted from each of the piezoelectric elements 10. More specifically, as shown in FIG. 7, the lower electrode wire section 22 of each of the piezoelectric elements 10 continues from the lower electrode main body section 21 and comprises an element connecting wire 221 configured to straddle the inside and outside of the membrane 121 and a lower electrode wire 222 connected from the element connecting wire 221 to the lower electrode terminal section 23. Since a plurality of the lower electrode wires 222 are formed between the membranes 121 of the piezoelectric elements 10, the lower electrode wires 222 are formed to have a smaller line width dimension than the element connecting wires 221 due to layout constraints. Consequently, the electrical resistance of the lower electrode wires 222 is larger than the electrical resistance of the element connecting wires 221.

With such an ultrasonic transducer 1, if over-etching of the lower electrode wires 222 occurs when the piezoelectric material and the upper electrode layer 50 of the piezoelectric elements 10 are fabricated, then the electrical resistance will increase and it will be necessary to apply a higher voltage in order to emit an ultrasonic wave having the desired sound pressure from the piezoelectric elements 10. However, in this embodiment, the second piezoelectric layers 40 are formed over the lower electrode wires 222, which have smaller line widths than the element connecting wires 221. Consequently, the lower electrode wires 222 are not over-etched when the transducer is being manufactured and an increase of the electrical resistance is suppressed.

In the ultrasonic transducer 1 according to the fourth embodiment, the upper electrode wire section 52 is configured such that, for example, there is a common upper electrode wire section 52 provided with respect to piezoelectric elements 10 arranged along a single direction as shown in FIG. 7 (a horizontal direction in the plane of the paper in FIG. 7). These upper electrode wire sections 52 are formed over the second piezoelectric layers 40 in the same manner as in the third embodiment. Consequently, the upper electrode wire sections 52 and the lower electrode wires 222 can be arranged closely adjacent to each other in a plan view such that the upper electrode wire sections 52 and the lower electrode wires 222 do not contact each other. With this configuration, the piezoelectric elements 10 can be arranged with short intervals in-between and the size of the substrate 11 of the ultrasonic transducer 1 can be made smaller. In the example shown in FIG. 7, the lower electrode wires 222 and the upper electrode wire sections 52 are arranged such that they do not overlap each other in a plan view, but it is acceptable to arrange the lower electrode wires 222 and the upper electrode wire sections 52 in such positions that they do overlap each other in a plan view.

Although in this embodiment the upper electrode wire sections 52 are used as common wires between the piezoelectric elements 10, it is also possible to use, for example, the lower electrode wires 222 as common wires. In such a case, the lower electrode wires 222 can be made to have a larger line width dimension and can be protected from over-etching during manufacturing by the second piezoelectric layers 40 provided thereon. As a result, an increase of the electrical resistance can be suppressed even more reliably. The piezoelectric elements 10 are arranged at a constant pitch Px along a horizontal direction (first direction) from the perspective of FIG. 7. The piezoelectric elements 10 are also arranged at a constant pitch Py along a vertical direction (second direction) from the perspective of FIG. 7. Thus, an array structure is obtained in which the piezoelectric elements 10 are arranged at constant pitches in two perpendicular directions and an echo image can be acquired when this structure is used in an ultrasonic probe. Additionally, it is acceptable to make the values of the pitches Px and Py the same. Using equal pitches enables an echo image with less distortion to be acquired.

Operational Effects of Fourth Embodiment

The ultrasonic transducer 1 according to the fourth embodiment has an array structure in which a plurality of piezoelectric elements 10 are arranged in rows and columns. With such an ultrasonic transducer 1, it is necessary to arrange a plurality of lower electrode wires 222 between the piezoelectric elements 10 when forming the lower electrode wire section 22 on the substrate 11 and the width dimensions of the lower electrode wires 222 are restricted, thus causing the electrical resistance thereof to increase. If the lower electrode wires 222 are over-etched when the ultrasonic transducer 1 is manufactured, then the electrical resistance will increase further and the sound pressure of the ultrasonic waves produced will decline, making it difficult to drive and control the ultrasonic transducer 1 in a high frequency region. With this embodiment, however, since the second piezoelectric layers 40 are formed over the lower electrode wires 222, the lower electrode wires 222 can be protected from over-etching during manufacturing and the increase of the electrical resistance can be suppressed.

Also, since the second piezoelectric layers 40 are formed over the upper electrode wire sections 52, the lower electrode wires 222 and the upper electrode wire sections 52 can be prevented from contacting each other. Thus, the lower electrode wires 222 and the upper electrode wire sections 52 can be arranged in such positions that they overlap in a plan view, the distances between piezoelectric elements 10 can be shortened, and the size of the ultrasonic transducer 1 can be reduced.

Device Example 1

Figure 8:
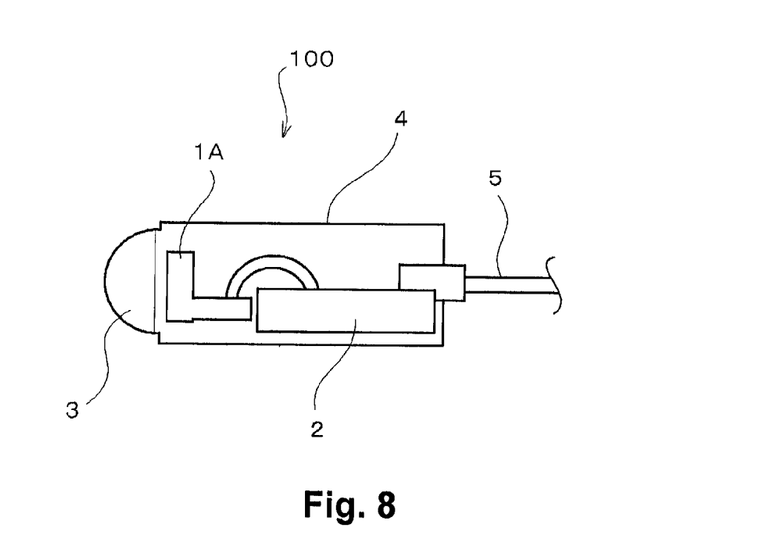
FIG. 8 is a schematic view of an ultrasonic probe according to the present invention in the form of a device.
Figure 9:
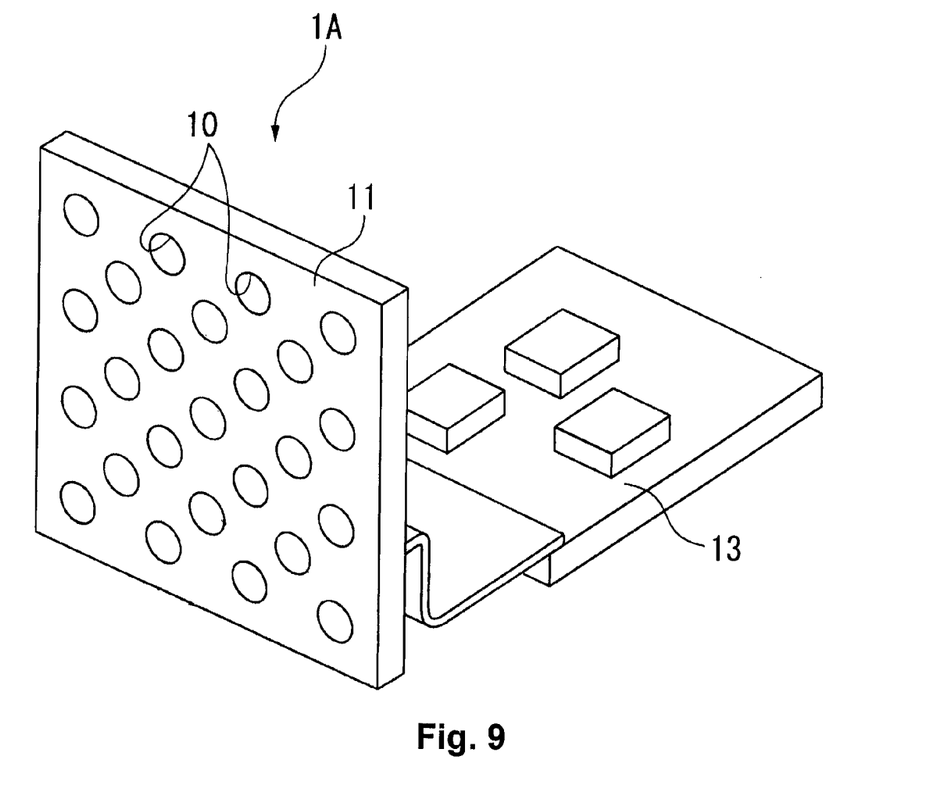
FIG. 9 is a simplified perspective view of an ultrasonic transducer used in an ultrasonic probe according to the present invention.

As an example of a device, a medical instrument equipped with a piezoelectric element 10 according to the embodiments as explained previously will now be explained. In this example, the medical instrument is an ultrasonic probe. FIG. 8 is a simplified perspective view showing an ultrasonic probe 100 according to the device example. FIG. 9 is a simplified perspective view showing an ultrasonic transducer 1A used in this ultrasonic probe.

As shown in FIG. 8, the ultrasonic probe 100 has the ultrasonic transducer 1A, a drive circuit 2 that drives the ultrasonic transducer 1A, an acoustic lens 3 provided in a position separated from the ultrasonic transducer 1A along the direction in which the ultrasonic transducer 1A emits ultrasonic waves, a case 4, and a cable 5.

As shown in FIG. 9, the ultrasonic transducer 1A comprises a plurality of ultrasonic wave transmitting piezoelectric elements 10 arranged on a substrate 11. Similarly to the ultrasonic transducer 1 of the fourth embodiment, these piezoelectric elements 10 are arranged in an array structure like that shown in FIG. 7 and second piezoelectric layers 40 are laminated over the lower electrode wires 222, which are arranged in a region of the lower electrode wire section 22 located outside the membrane 121. A computer control section 13 is connected to the substrate 11 to control the piezoelectric elements 10.

In this ultrasonic transducer, the second piezoelectric layers 40 are formed over the lower electrode wires 222 formed in a region of the lower electrode wire sections 22 lying outside the membranes 121. Consequently, the lower electrode wires 222 are not over-etched during manufacture and an increase of electrical resistance caused by over-etching is avoided. As a result, the ultrasonic wave transmitting piezoelectric elements 10A can transmit ultrasonic waves having a large sound pressure using a smaller drive voltage. Moreover, with the ultrasonic wave receiving piezoelectric elements 10B, attenuation of the electrical signal outputted in response to receiving an ultrasonic wave can be suppressed. In other words, the ultrasonic transducer 1A can transmit and receive ultrasonic waves with good accuracy and electric power can be conserved. As a result, an ultrasonic probe equipped with such an ultrasonic transducer 1A can acquire an accurate image of the interior of a test object while suppressing electric power consumption.

In the device example just explained, a piezoelectric element according to the above described embodiments is employed in a transmitter/receiver device of an ultrasonic probe 100 that incorporates the ultrasonic transducer 1A. This device is not limited to medical instruments and can also be used as a probe for a distance measuring sensor, a sensor for non-destructive inspection of pipes, or a measuring sensor for monitoring a flow rate of a fluid in a pipe.

Device Example 2

Figure 10:
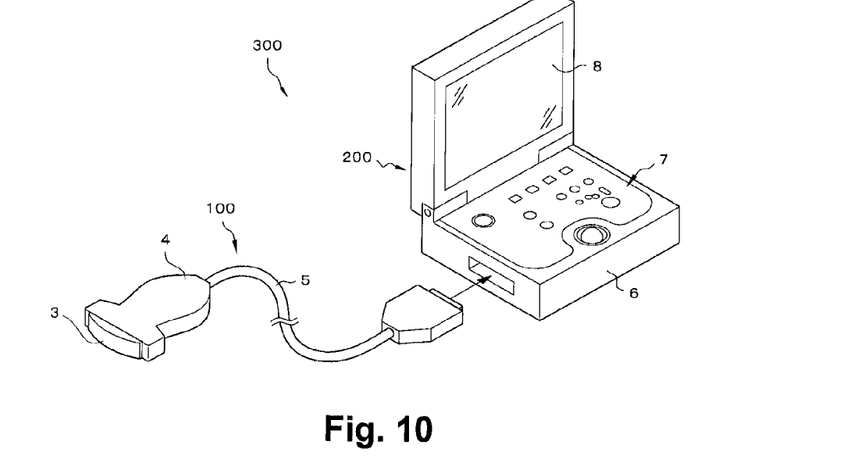
FIG. 10 is a schematic view of an ultrasonic image diagnostic device according to the present invention.

An ultrasonic image diagnostic device will now be explained as a second device example according to the present invention. FIG. 10 shows an ultrasonic image diagnostic device 300. The ultrasonic probe 100 is connected to a device main body 6 of an ultrasonic wave observer 200. An operator sets a drive condition of the ultrasonic probe 100 using an operating section 7 and an echo image is displayed on a display monitor 8.

Other Embodiments

The present invention is not limited to the previously explained embodiments, and various changes and improvements can be made without departing from the scope of the invention as defined by the claims.

For example, in the previously explained embodiments, the second piezoelectric layer 40 covers a portion of the lower electrode layer 20 spanning from the end position 22A located at a distance L from the edge 111A of the opening section 111 to the connecting section 22B where the lower electrode wire section 22 connects to the lower electrode terminal section 23. However, it is acceptable for the second piezoelectric layer 40 to cover, for example, from the edge 111A of the opening section 111 to the connecting section 22B. In either case, the resistance with respect to deflection of the membrane 121 can be decreased in comparison with a configuration in which the second piezoelectric layer 40 spans across the inside and outside of the opening section 111.

It is also acceptable for the second piezoelectric layer 40 to be formed on a portion of the edge 111A of the opening section 111. For example, it is acceptable for the second piezoelectric layer 40 to be formed across the inside and outside of the opening section by straddling the edge 111A of the opening section 111 only at the position where the lower electrode wire section 22 is formed. In such a case, since there are no portions of the lower electrode wire section 22 exposed to the outside, over-etching of the lower electrode wire section 22 can be reliably prevented when the piezoelectric layer 60 and the upper electrode layer 50 are etched and an increase of the electrical resistance can be reliably suppressed. Also, compared to a configuration in which the second piezoelectric layer 40 is formed over the entire circumference of the edge 111A of the opening section 111, the increase of the resistance with respect to deflection of the membrane 121 is negligible and ultrasonic waves having a large sound pressure can be produced.

It is also acceptable for the second piezoelectric layer 40 to be formed in all regions except in the area within the distance L from the edge 111A of the opening section 111, which is the area where there is a risk of inhibiting vibration of the membrane 121.

Although in the previously explained embodiments the lower electrode layer 20 is formed on the support film 12, the invention is not limited to such a configuration. For example, it is acceptable for the support film 12 to be etched, another layer (e.g., an insulation layer) to be deposited onto the etched portion, and the lower electrode layer 20 to be formed on the other layer.

The preferred embodiments of the present invention have been explained in detail herein, but the invention is not limited to these configurations. Although the present invention has been explained and depicted in the drawings chiefly in relation to specific embodiments, those skilled in the art can apply various changes and improvements to the previously explained embodiments without departing from the technical concepts and objects of the invention.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic probe comprising:
   a piezoelectric element including
      a support body having an opening section and a displacement section covering the opening section on one side of the support body,
      a lower electrode layer disposed over the one side of the support body and continuously extending from an inside of an overlap area of the displacement section with the opening section to an outside of the overlap area when viewed in a plan view along a thickness direction of the support body,
      a first piezoelectric layer disposed over the lower electrode layer, and positioned inside of the overlap area when viewed in the plan view,
      an upper electrode layer disposed over the first piezoelectric layer, and
      a second piezoelectric layer disposed over the lower electrode layer, apart from the first piezoelectric layer when viewed in the plan view.

2. The ultrasonic probe according to claim 1, wherein
the support body includes a substrate having the opening section and a support film disposed over the one side of the substrate so that a portion of the support film covering the opening section forms the displacement section.

3. The ultrasonic probe according to claim 1, wherein
the second piezoelectric layer is spaced apart from the first piezoelectric layer.

4. The ultrasonic probe according to claim 1, wherein
the lower electrode layer has a lower electrode main body section, over which the first piezoelectric layer is disposed, and a lower electrode wire section continuously extending from the lower electrode main body section over the one side of the support body when viewed in the plan view, and
the second piezoelectric layer is disposed over the lower electrode wire section.

5. The ultrasonic probe according to claim 1, wherein
the second piezoelectric layer is disposed at a position that does not overlap the opening section when viewed in the plan view.

6. The ultrasonic probe according to claim 1, further comprising
a wiring layer disposed over the second piezoelectric layer and connected to the lower electrode layer.

7. The ultrasonic probe according to claim 1, further comprising
a wiring layer disposed over the second piezoelectric layer and connected to the upper electrode layer.

8. The ultrasonic probe according to claim 4, wherein
the lower electrode wire section includes
   an element connecting wire connected to the lower electrode main body section and continuously extending on the one side of the support body, and
   a lower electrode wire extending from the element connecting wire and positioned on the one side of the support body when viewed in the plain view, the lower electrode wire having a narrower line width than a line width of the element connecting wire, and
the second piezoelectric layer is disposed over the lower electrode wire of the lower electrode wire section.

9. The ultrasonic probe according to claim 1, wherein
a plurality of the piezoelectric elements are arranged at a constant pitch along a first direction and at a constant pitch along a second direction perpendicular to the first direction.

10. The ultrasonic probe according to claim 9, wherein
the pitch at which the piezoelectric elements are arranged along the first direction and the pitch at which the piezoelectric elements are arranged along the second direction are the same.

11. An ultrasonic image diagnostic device comprising:
an ultrasonic wave observer including a device main body; and
an ultrasonic probe connected to the device main body, the ultrasonic probe including a piezo electric element including a support body having an opening section and a displacement section covering the opening section on one side of the support body, a lower electrode layer disposed over the one side of the support body and continuously extending from an inside of an overlap area of the displacement section with the opening section to an outside of the overlap area when viewed in a plan view along a thickness direction of the support body, a first piezoelectric layer disposed over the lower electrode layer, and positioned inside of the overlap area when viewed in the plan view, an upper electrode layer disposed over the first piezoelectric layer, and a second piezoelectric layer disposed over the lower electrode layer, apart from the first piezoelectric layer when viewed in the plan view.

12. The ultrasonic image diagnostic device according to claim 11, wherein
the support body includes a substrate having the opening section and a support film disposed over the one side of the substrate so that a portion of the support film covering the opening section forms the displacement section.

13. The ultrasonic image diagnostic device according to claim 11, wherein
the second piezoelectric layer is spaced apart from the first piezoelectric layer.

14. The ultrasonic image diagnostic device according to claim 11, wherein
the lower electrode layer has a lower electrode main body section, over which the first piezoelectric layer is disposed, and a lower electrode wire section continuously extending from the lower electrode main body section over the one side of the support body when viewed in the plan view, and
the second piezoelectric layer is disposed over the lower electrode wire section.

15. The ultrasonic image diagnostic device according to claim 11, wherein
the second piezoelectric layer is disposed at a position that does not overlap the opening section when viewed in the plan view.

16. The ultrasonic image diagnostic device according to claim 11, wherein
a wiring layer disposed over the second piezoelectric layer and connected to the lower electrode layer.

17. The ultrasonic image diagnostic device according to claim 11, wherein
a wiring layer disposed over the second piezoelectric layer and connected to the upper electrode layer.

18. The ultrasonic image diagnostic device according to claim 14, wherein
the lower electrode wire section includes
an element connecting wire connected to the lower electrode main body section and continuously extending on the one side of the support body, and
a lower electrode wire extending from the element connecting wire and positioned on the one side of the support body when viewed in the plain view, the lower electrode wire having a narrower line width than a line width of the element connecting wire, and
the second piezoelectric layer is disposed over the lower electrode wire of the lower electrode wire section.

19. The ultrasonic image diagnostic device according to claim 11, wherein
a plurality of the piezoelectric elements are arranged at a constant pitch along a first direction and at a constant pitch along a second direction perpendicular to the first direction.

20. The ultrasonic image diagnostic device according to claim 19, wherein
the pitch at which the piezoelectric elements are arranged along the first direction and the pitch at which the piezoelectric elements are arranged along the second direction are the same.

\* \* \* \* \*